(12) United States Patent
Azzaretto

(10) Patent No.: US 6,537,066 B1
(45) Date of Patent: Mar. 25, 2003

(54) SUPPORTING PLATE FOR A DENTURE MODEL

(76) Inventor: Michael Azzaretto, 55C, Rue de Metz, 57470 Hombourg-Haut (FR)

( * ) Notice: Subject to any disclaimer, the term of this patent is extended or adjusted under 35 U.S.C. 154(b) by 0 days.

(21) Appl. No.: 09/787,704
(22) PCT Filed: Jul. 20, 2000
(86) PCT No.: PCT/DE00/02415
§ 371 (c)(1),
(2), (4) Date: May 14, 2001
(87) PCT Pub. No.: WO01/06945
PCT Pub. Date: Feb. 1, 2001

(30) Foreign Application Priority Data

Jul. 21, 1999 (DE) .......................... 199 34 268

(51) Int. Cl.⁷ .............................................. A61C 19/00
(52) U.S. Cl. ........................................................ 433/34
(58) Field of Search ..................................... 433/34, 74

(56) References Cited

U.S. PATENT DOCUMENTS

| | | | | |
|---|---|---|---|---|
| 4,283,173 A | * | 8/1981 | Browne et al. | 433/34 |
| 4,767,330 A | * | 8/1988 | Burger | 433/213 |
| 5,154,610 A | * | 10/1992 | Gregorio Gracia | 433/74 |
| 5,506,095 A | * | 4/1996 | Callne | 433/34 |
| 5,996,963 A | * | 12/1999 | Michael | 433/54 |
| 6,099,305 A | * | 8/2000 | Browne et al. | 433/34 |
| 6,149,428 A | * | 11/2000 | Mogensen | 433/74 |

* cited by examiner

Primary Examiner—John J. Wilson
(74) Attorney, Agent, or Firm—Sofer & Haroun, LLP

(57) ABSTRACT

The invention relates to a supporting plate with retention pins for a denture model which makes it possible to repeatedly remove the denture model or individual jaw tooth segments from the supporting plate or to exactly put back the denture model or individual denture model segment on the supporting plate without wearing out by friction the material of the model. This is achieved by means of a supporting plate for a denture model in which the height of the outer side wall of the arc-shaped impression on the supporting plate is lower in height relative to the inner side wall, and where the outer side wall is vertical or diagonal. Furthermore, wall segments having different contours make it possible to easily and rapidly classify the removed denture model segments.

14 Claims, 2 Drawing Sheets

SUPPORTING PLATE FOR A DENTURE MODEL

Figure 1:
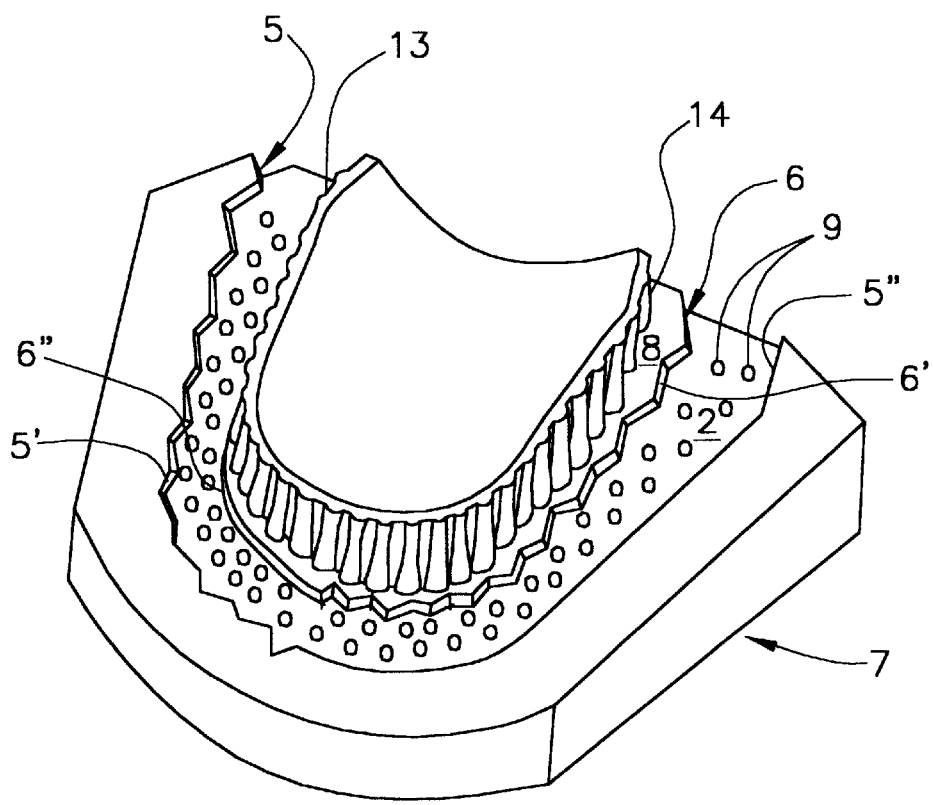

The invention relates to a supporting plate for a denture model.

To manufacture dentures, e.g. crowns, bridges, inlays and the like, the dental technicien needs a positive model of the patient's jaws and teeth. For that purpose the negative molds of the upper and lower jaw of the patient, supplied by the dentist, are filled with a mold material, e.g. plaster of paris, and covered with a supporting plate with retention pins extending into the mold material which remain in the mold material after hardening. After hardening of the mold material and removal of the negative mold a positive model of the patient's upper or lower jaw is available on a supporting plate.

This positive denture model with its supporting plate is placed together with the respective counter jaw model of the patient into a jaw movement simulator (articulator) allowing to simulate individual jaw movements of the patient. This procedure allows to manufacture dentures exactly matching the patient's own teeth and jaw positions and movements.

For the final modelling the denture model on the supporting plate has to be removed from and put back on the supporting plate. Very often the denture model has to be sawn into various jaw or tooth segments to make final modelling of this segment easier. For that pupose the denture model is detached together with the retention pins from the supporting plate and then sawn into individual segments.

After that the individual denture segments are put back on the supporting plate using the retention pins to place the segments as exactly as possible into their former position so that they are solidly secured on the supporting plate even in the case if the supporting plate is to be inserted into the upper part of an articulator with a row-of teeth of the denture model facing downwards.

According to the PCT Patent Specification WO 98/10709 a supporting plate for a denture model is given in which the side walls of the arc-shaped impression in the upper side have vertical grooves and where the bottom is to be equipped with a plurality of bore holes with inserted retention pins.

The retention pins are made of plastic and would be cut, too, when saw cuts are made in the denture model to obtain individual jaw or tooth segments, so that sawing becomes difficult, and partly sawn retention pins are remaining.

Another disadvantage of the known supporting plate is that all retention pins inserted in the bore holes in the bottom of the impression of the supporting plate become stuck in the hardened denture model and cannot be removed so that it becomes difficult to remove the denture model or individual jaw or tooth segments from the supporting plate or to put back the denture model or individual denture model segments on the supporting plate, the tilting of the retention pins in the bore holes and the angular position of the denture model or individual segments during removal or putting back leading to wearing out by friction or cracks of the mold material.

After hardening of the liquid mold material, e.g. plaster of paris, poured in the negative mold of a patient's jaw and teeth and on which the supporting plate of the known design has been placed before hardening, the positive denture model removed from the impression in the supporting plated shows on its outer walls a ribbed structure corresponding to the grooves in the impression of the denture model so that the ribs in the outer wall of the denture model or of the segments mate the grooves in the side walls of the impression of the denture model when the denture model or the jaw and tooth segments are put back on the supporting plate.

However, the disadvantage is that the edges of the denture model or its denture model segments are considerably worn out by friction when the denture model is removed from the supporting plate and the denture model or individual denture model segments are put back or removed on repeated occasions.

The edges of the denture model, usually made of plaster of paris, are also worn out by friction or can chip off when a denture model segment is put back in the wrong place of the denture model in the impression of the supporting plate.

However, even the smallest damage on denture model and jaw or tooth segments, e.g. due to chipped-off edges or mold material worn out by friction will endanger the proper sitting of the denture model or segments on the supporting plate, so that the dentures manufactured according to the denture model will later on sit badly in the mouth of the patient.

The invention provides for the construction of a supporting plate for a denture model which makes it possible to repeatedly remove the denture model or individual jaw or tooth segments from the supporting plate and to exactly put back the denture model or individual denture model segments on the supporting plate without wearing out by friction the mold material.

This is achieved by means of a supporting plate for a denture model in which the height of the outer side wall of the arc-shaped impression on the supporting plate is considerably reduced—by approximately 4/5- and the outer side wall is vertical or slanted.

It is an advantage that the inner side wall of the arc shaped impression on the supporting plate has a stepped-shaped ridge at the level of the remaining opposed outer side wall of the arc-shaped impression, the ridge's side wall is vertical or slanted, and the vertical or slanted side wall of the stepped-shaped ridge of the inner side wall and the outer side wall of the arc-shaped impression on the supporting plate have different contours along half of each length, the wall segments with different contours being opposite to each other.

It is useful that the vertical grooves of the remaining inner side wall above the step-shaped ridge are narrowing downwards.

In a different version of the invention the ribs between the vertical grooves narrowing downwards are widening downwards.

In another version of the invention the retention pins inserted in the bore holes are threaded at their upper ends extending into the arc-shaped impression on the supporting plate.

It is useful that the retention pins have a recess at their ends protruding from the lower side of the supporting plate.

One version of the invention is explained and described in greater detail below with the help of drawings.

Figure 3:
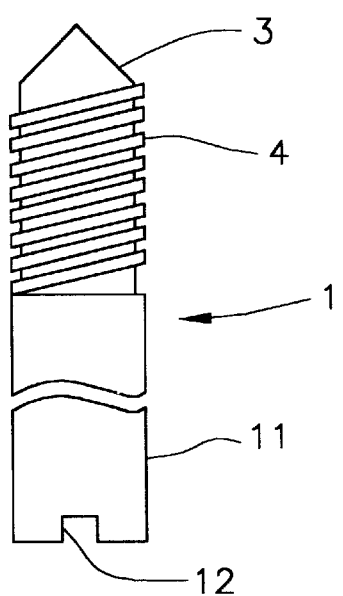
Figure 2:
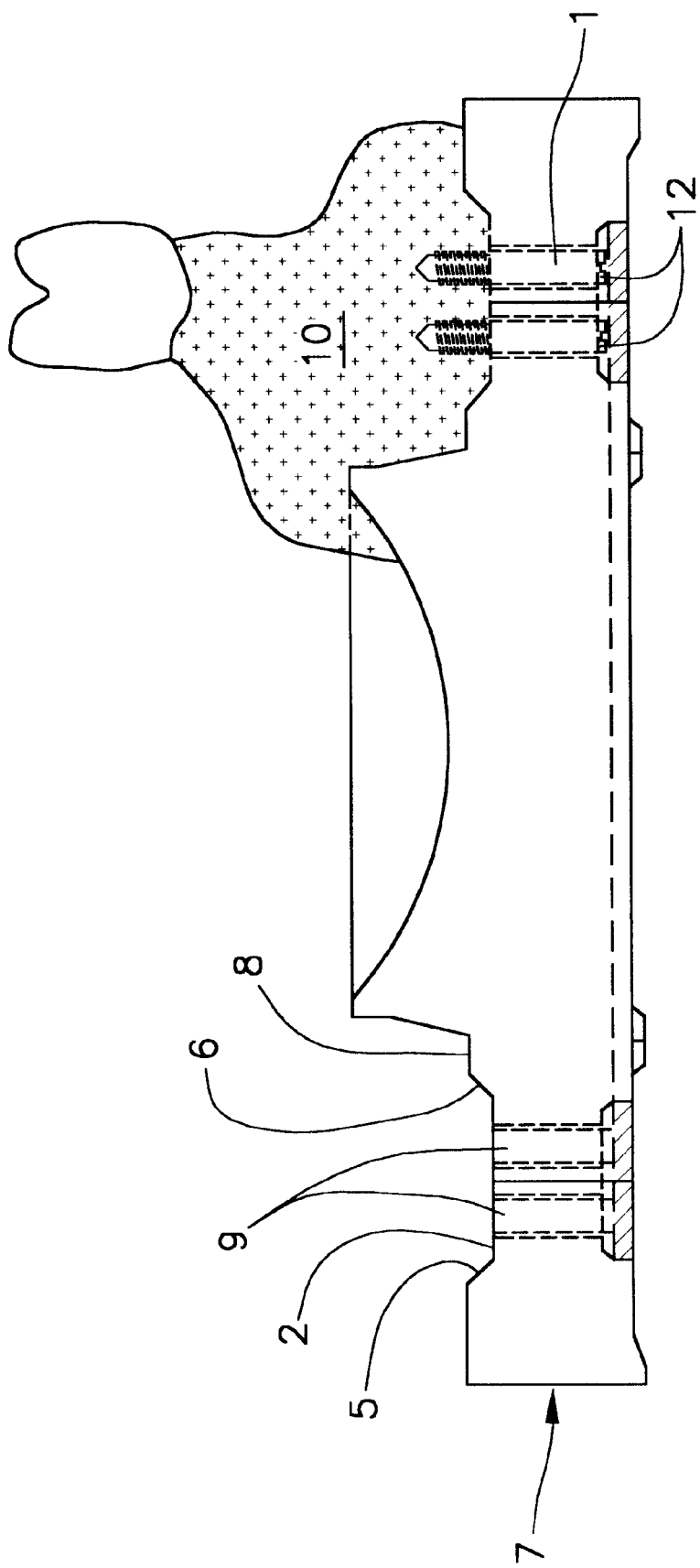

FIG. 1 is a top prospective view of the supporting plate for a denture model, of about natural size, FIG. 2 is a side view of the object shown in FIG. 1, and FIG. 3 shows a retention pin, about 10 times the natural size.

FIG. 1 and FIG. 2 represent a supporting plate according to the invention in which the height of the outer side wall 5 of the arc-shaped impression 2 with the bore holes 9,9,9 . . . on the supporting plate 7 is reduced by approximately 4/5 and slanted.

The inner side wall 6 has a step-shaped ridge 8 at the level of the opposed side wail 5.

The vertical or slanted side wall of the stepped shaped ridge 8 of the inner side wall 6 and the outer side wall 5 have different contours along half of each length 5', 5"; 6', 6", the wall segments of the inner and outer side walls 6, 5 with different contours 5', 6":5", 6' being opposite to each other.

The reduction in height of the outer side wall 5 makes it possible to remove the denture model 10 or individual denture model segments from the supporting plate 7 or to put them back without wearing out by friction the mold material along the edges of the denture model 10 or individual segments.

The different wall contours of the inner and outer side walls 5, 6 make it impossible to put the jaw or tooth segments by mistake back into a wrong position of the supporting plate because the easily and rapidly discernable different segments contours allow to rapidly classify the denture model segment. This avoids the wearing out by friction along the edges of the denture model segments due to the improper re-insertion and removal.

In FIG. 1 the vertical groove 13 on the inner side wall 6 are narrowing downwards. The ribs 14 between the grooves 13 are parallel in their upper part and widening downwards.

FIG. 3 shows a retention pin to be inserted half-way into a bore hole 9 in the bottom of the arc-shaped impression 2 on the supporting plate 7 and having on its upper end 3 a thread 4.

This thread 4 extends into the hardened mold material of the denture model 10 where it is kept hold.

The lower bare end 11 of the retention pin 1 which can have a cylindrical, conical or any other shape, is placed into the suitibly shaped bore hole 9 when the denture model 10 is placed on the supporting plate 7.

In order to reduce the retention pins 1,1,1 . . . remaining in the denture model 10 to the minimum number of retention pins 1,1,1 . . . necessary to secure the denture model 10 or individual denture model segments on the supporting plate 7, any unnecessary retention pins 1,1,1 . . . are removed from denture model 10.

The removed retention pins 1,1,1 . . . can be reused for the assembly of a new supporting plate.

The recess 12 at the lower end 11 of the retention pin 1 allows to easily remove the rention pin 1 from the denture model 10 by means of a screw driver. Should a wrong retention pin 1 have been removed, it can be easily re-inserted in the same position in the denture model 10 using a screw driver.

What is claimed is:

1. A supporting plate for a denture model, said plate comprising;

an arc-shaped impression on an upper side of the plate;

outer and inner sidewalls on said upper surface of the plate disposed on either side of said arc-shaped impression, at least one of said outer and inner side walls having vertical grooves thereon; wherein the height of said outer side wall of said arc shaped-impression is substantially lower than the height of said inner side wall so as to allow removal of said denture model without friction; and bore holes adapted to receive retention pins, said bore holes disposed within the plate.

2. A supporting plate for a denture model as claimed in claim 1, wherein said outer side wall is vertical.

3. A supporting plate for a denture model as claimed in claim 1, wherein said outer side wall is slanted.

4. A supporting plate for a denture model as claimed in claim 1, wherein said inner side wall of said arc-shaped impression disposed on said upper side of the plate has a step shaped ridge disposed at substantially the same level of said opposed outer side wall of said arc shaped impression.

5. A supporting plate for a denture model as claimed in claim 4, wherein said step shaped ridge of said inner side wall is vertical relative to said arc-shaped impression.

6. A supporting plate for a denture model as claimed in claim 4, wherein said step shaped ridge of said inner side wall is slanted.

7. A supporting plate for a denture model as claimed in claim 4, wherein said inner and outer side walls of said arc-shaped impression on said upper side of the plate have different contours along half of each length of wall segments, whereby differently contoured said wall segments of said inner side wall and said outer side wall are opposite to each other.

8. A supporting plate for a denture model as claimed in claim 4, further comprising vertical grooves disposed on said inner side wall on the portion above said step-shaped ridge.

9. A supporting plate for a denture model as claimed in claim 8, wherein said vertical grooves are wider at an upper end and narrower at said lower end.

10. A supporting plate for a denture model as claimed in claim 8, further comprising rips disposed between each said vertical groove located on said inner side wall.

11. A supporting plate for a denture model as claimed in claim 10, where in said rips are narrow at said upper said end of said inner side wall and wider at said lower end.

12. A supporting plate for a denture model as claimed in claim 1, wherein said bore holes have retention pins inserted therein.

13. A supporting plate for a denture model as claimed in claim 12, wherein said retention pins inserted into said bore holes have a thread disposed on their upper end extending into said arc-shaped impression of the plate.

14. A supporting plate for a denture model as claimed in claim 12, wherein said retention pins inserted into said bore holes have a recess at their lower ends protruding from the lower side of the plate.

\* \* \* \* \*